United States Patent [19]
Aoki et al.

[11] Patent Number: 5,362,967
[45] Date of Patent: Nov. 8, 1994

[54] PNEUMATIC INFRARED RAY DETECTOR FOR USE IN GAS ANALYZER

[75] Inventors: Junji Aoki; Kazuhide Mukaihara, both of Miyanohigashi, Japan

[73] Assignee: Horiba, Ltd., Kyoto, Japan

[21] Appl. No.: 127,004

[22] Filed: Sep. 24, 1993

[30] Foreign Application Priority Data

Sep. 30, 1992 [JP] Japan ............................ 4-074419[U]
Sep. 30, 1992 [JP] Japan ............................ 4-286961

[51] Int. Cl.⁵ .................................... G01N 21/61
[52] U.S. Cl. ............................ 250/344; 250/343
[58] Field of Search ............ 250/344, 343, 345, 341, 250/339

[56] References Cited
U.S. PATENT DOCUMENTS

| | | | |
|---|---|---|---|
| 3,968,369 | 7/1976 | Luft | 250/344 |
| 4,201,915 | 5/1980 | Schunk et al. | 250/343 |
| 4,306,150 | 12/1981 | Dietz | 250/340 |
| 4,742,229 | 5/1988 | Weinel | 250/344 |

Primary Examiner—Paul M. Dzierzynski
Assistant Examiner—Richard Aanig
Attorney, Agent, or Firm—Poms, Smith, Lande & Rose

[57] ABSTRACT

A pneumatic infrared ray detector for use in a gas analyzer provided with a gas-slowly leaking mechanism capable of not only controlling a quantity of gas leaked in high accuracy but also increasing a range capable of controlling said quantity of gas leaked is provided. A body is provided with gas chambers and a detecting gas chamber and the respective gas chambers are communicated with said detecting gas chamber through gas passages. A ring-shaped leak-controlling sheet on the bottom surface of the detecting gas chamber is provided with a groove-like gas-leaking passage between the inner and outer circumferential edges thereof and a ring-shaped diaphragm and a vibrating diaphragm are built up on said leak-controlling sheet to be fixedly pressurized by means of a cover plate through a pressurizing member and a plate spring.

21 Claims, 5 Drawing Sheets

5,362,967

PNEUMATIC INFRARED RAY DETECTOR FOR USE IN GAS ANALYZER

BACKGROUND OF THE INVENTION

1. Field of the Invention

The present invention relates to a pneumatic infrared ray detector for use in a gas analyzer detecting infrared rays transmitting through a sample cell and the like to be incident upon a gas chamber.

2. Description of the Prior Art

A pneumatic infrared ray detector for use in a gas analyzer comprises for example a gas chamber, upon which infrared rays transmitting through a sample gas are incident, and a gas chamber, upon which infrared rays transmitting through a reference gas are incident, provided separately, a pair of said gas chambers being communicated with each other through a gas passage, and said gas passage being cut off by means of a vibrating diaphragm of a condenser microphone. And, if there is a difference between said infrared rays incident upon one of the gas chambers and said infrared rays incident upon the other of the gas chambers in quantity, a difference corresponding to said difference in quantity of light is produced between both sides of said vibrating diaphragm in gas pressure, so that, in order to balance these gas pressures, a mechanism for slowly leaking a gas within one of said gas passages cut off by means of the vibrating diaphragm to the other of the gas passages is provided. And, a quantity of said gas slowly leaked becomes an important factor determining a sensitivity and frequency characteristics of said detector, so that it has been required that said quantity of the gas slowly leaked can be controlled in high accuracy.

The pneumatic infrared ray detector for use in a gas analyzer shown in, for example, FIGS. 9, 10 has been known. Referring to FIGS. 9, 10, reference numeral 1 designates a body made of metals and the like provided with a pair of independent gas chambers 2a, 2b, respective opened portions of said gas chambers 2a, 2b, being closed by means of an incident window (not shown) made of infrared ray-transmissive optical material, and a gas being enclosed in the respective gas chambers 2a, 2b. Reference numeral 3 designates a detecting gas chamber provided independently upon the gas chambers 2a, 2b and reference numeral 4 designates a gas passage provided ranging from the gas chamber 2a to a circumferential wall surface of said detecting gas chamber 3 for communicating the gas chamber 2a with the detecting gas chamber 3. Reference numeral 5 designates a gas passage provided ranging from a position distant from a circumferential wall to the gas chamber 2b in a bottom surface 3a of the detecting gas chamber 3 for communicating the gas chamber 2b with the detecting gas chamber 3.

Reference numeral 6a designates a ring-shaped slow leak sheet made from a thin sheet built up on said bottom surface 3a of the detecting gas chamber 3 and an end portion of said gas passage 5 is opened on an inner circumferential side of said ring-shaped slow leak sheet 6a. Reference numeral 8 designates a ring-shaped member built up on the slow leak sheet 6a and a surface brought into contact with the slow leak sheet 6a of said ring-shaped member 8 is roughened. A rough surface of the member 8 is formed by grinding with grinding materials and the like. Reference numeral 9 designates a gas gap formed on an inner circumferential side of the slow leak sheet 6a and the member 8 in their thicknesses.

Reference numeral 10 designates a vibrating diaphragm made from a titanium foil and the like composing a condenser microphone built up on the member 8. Reference numeral 11 designates a pressurizing member made from insulating materials built up on said vibrating diaphragm 10, said pressurizing member 11 being provided with a concave portion 12 formed at a central side portion of a surface opposite to the vibrating diaphragm 10 thereof, said concave portion 12 being provided with a gas hole 13 formed in a circumferential portion thereof, and a fixed electrode 14 being fixedly mounted in opposition to the vibrating diaphragm 10.

Reference 15 designates a ring-shaped and wave-shaped plate spring built up on the pressurizing member 11 and reference numeral 16 designates a cover plate. The detecting gas chamber 3 is closed up tight by means of said cover plate 16. The pressurizing member 11, the vibrating diaphragm 10, the member 8 and the slow leak sheet 6a are pressurized through said plate spring 15, respectively, to bring them into close contact with each other at their respective contact surfaces. Accordingly, the gas passages 2a, 2b opened to the detecting gas chamber 3 at one end thereof are cut off by means of the vibrating diaphragm 10. However, a small gap is produced at a contact surface of the slow leak sheet 6a and the member 8 due to said rough surface of the member 8; it is possible to slowly leak the gas in their inner and outer circumferential directions. The plate spring 15 can produce a gas-flowing gap between the pressurizing member 11 and the cover plate 16 and flow the gas in inner and outer circumferential directions of the plate spring 15. Accordingly, of the respective gases enclosed in the gas chambers 2a, 2b, the gas enclosed in the gas chamber 2a arrives at the detecting gas chamber 3 through the gas passage 4 to be filled in the concave portion 12 closed up tight by means of the vibrating diaphragm 10 through said gas hole 13. On the other hand, the gas enclosed in the gas chamber 2b flows through the gas passage 5 to be filled in said gas gap 9 on one side of the vibrating diaphragm 10.

For example, when infrared rays transmitting through a reference gas of a gas analyzer are incident upon the gas chamber 2a and infrared rays transmitting through a sample gas are incident upon the gas chamber 2b, the former is larger in comparison with the latter in quantity of light. Accordingly, the vibrating diaphragm 10 is moved by a pressure resulting from an expansion of the gas enclosed in the gas chamber 2a and thus an electrostatic capacity of a condenser is changed, so that this change in electrostatic capacity is detected. And, upon acting said pressure resulting from said expansion of the gas enclosed in the gas chamber 2a upon the vibrating diaphragm 10 in the above described manner, a difference is produced between a gas pressure in the concave portion 12 on one side of the vibrating diaphragm 10 and that in the gas gap 9 on the other side of the vibrating diaphragm 10. Accordingly, the gas is slowly leaked between the detecting gas chamber 3 and the gas gap 9, as shown by, for example, an arrow in FIG. 9, at a contact surface of the slow leak sheet 6a and the member 8 due to this difference in gas pressure to absorb the difference in gas pressure between both sides of the vibrating diaphragm 10, whereby balancing the gas pressure.

In a slow leak mechanism in the above-described conventional pneumatic infrared ray detector for use in a gas analyzer, the rough surface of the member 8 is brought into contact with the slow leak sheet 6a to produce the gap resulting from the rough surface at the contact surface of the member 8 and the slow leak sheet 6a and these are pressed against each other to control the gap resulting from the rough surface, whereby slowly leaking the gas, that is it is possible to slowly leak the gas. However, the quantity of the gas leaked is controlled by changing a degree of roughness of the rough surface of the member 8, so that it is difficult to control the quantity of the gas leaked consciously in high accuracy. In addition, in the case where this quantity of the gas leaked is controlled to a great extent, it is required to increase said roughness of the rough surface but an increase of the roughness has a limit, so that a problem occurs also in that a range capable of controlling the quantity of the gas leaked is comparatively small.

SUMMARY OF THE INVENTION

The present invention solves the above-described problems and it is an object of the present invention to provide a pneumatic infrared ray detector for use in a gas analyzer capable of controlling a quantity of gas leaked in high accuracy and provided with a gas-slowly leaking mechanism capable of increasing a range capable of con-trolling said quantity of said gas leaked.

A pneumatic infrared ray detector for use in a gas analyzer, in which a pair of gas chambers, upon which infrared rays are incident, is provided in a body, a gas passage being formed for communicating said pair of gas chambers with each other, a vibrating diaphragm cutting off said gas passage being fixedly mounted on said body while all circumferential edge portion thereof is supported from both sides, and a mechanism for communicating the gas passages cut off by means of said vibrating diaphragm with each other to slowly leak gases enclosed in the respective gas chambers being provided, according to a first embodiment of the invention, is characterized in that a ring-shaped leak-controlling sheet built up all over the circumferential edge portion on one side of the vibrating diaphragm is provided with a groove-shaped gas-leaking passage formed all over the length between an inner circumferential edge and an outer circumferential edge thereof on a side surface thereof and one of the gas passages cut off by means of the vibrating diaphragm is provided on an outer circumferential side of said leak-controlling sheet while the other of the gas passages cut off by means of the vibrating diaphragm is provided on an inner circumferential side of the leak-controlling sheet.

A pneumatic infrared ray detector for use in a gas analyzer, in which a pair of gas chambers, upon which infrared rays are incident, is provided in a body, a gas passage being formed for communicating said pair of gas chambers with each other, a vibrating diaphragm cutting off said gas passage being fixedly mounted on said body while all circumferential edge portion thereof is supported from both sides, and a mechanism for communicating the gas passages cut off by means of said vibrating diaphragm with each other to slowly leak gases enclosed in the respective gas chambers being provided, according to a second embodiment of the invention, is characterized in that a ring-shaped, leak-controlling sheet built up all over the circumferential edge portion on one side of the vibrating diaphragm is provided with a groove-shaped, gas-leaking passage partially removed all over the length between an inner circumferential edge and an outer circumferential edge thereof and one of the gas passages cut off by means of the vibrating diaphragm is provided on an outer circumferential side of said leak-controlling sheet while the other of the gas passages cut off by means of the vibrating diaphragm is provided on an inner circumferential side of the leak-controlling sheet.

The leak-controlling sheet is made of metals, such as stainless steel and aluminum, Teflon (trade name) and the like. This leak-controlling sheet may be built up on one side of the vibrating diaphragm so as to be brought into immediate contact with it and may be built up on the circumferential portion of one side of the vibrating diaphragm with other members interposed between the vibrating diaphragm and the leak-controlling sheet.

In the above-described pneumatic infrared ray detector for use in a gas analyzer according to the present invention, the gas passages cut off by means of the vibrating diaphragm are communicated with each other through the gas-leaking passage formed in the leak controlling sheet. Accordingly, when the gas enclosed in one gas chamber is expanded due to the difference in quantity between the infrared rays incident upon the respective gas chambers to produce the difference in gas pressure between both sides of the vibrating diaphragm, the gas in one of the gas passages cut off by means of the vibrating diaphragm is slowly leaked through the gas-leaking passage to flow in the other gas passage, whereby balancing the gas pressures on both sides of the vibrating diaphragm. And, the quantity of the gas leaked through the gas-leaking passage can be determined depending upon a sectional area of the gas-leaking passage and said sectional area of the gas-leaking passage can be consciously and optionally set in high accuracy. Moreover, even if the leak-controlling sheet is pressurized from both sides thereof, the sectional area of the gas-leaking passage is hardly changed, so that not only the quantity of the gas slowly leaked can be controlled in high accuracy depending upon this sectional area but also the range capable of controlling the quantity of the gas to be leaked can be increased.

DETAILED DESCRIPTION OF THE PREFERRED EMBODIMENTS

Figure 1:
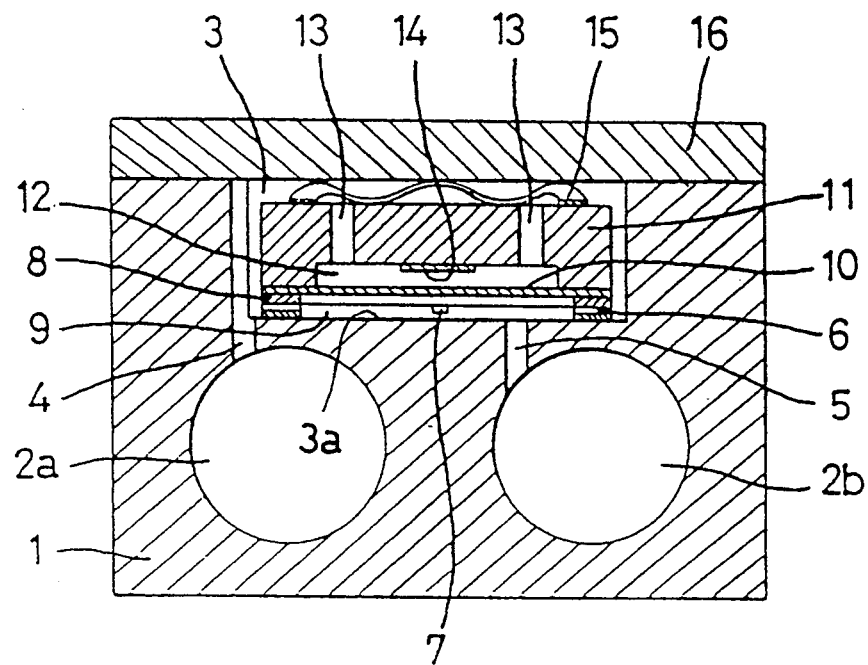
FIG. 1 is a block diagram showing a first preferred embodiment of the present invention.
Figure 2:
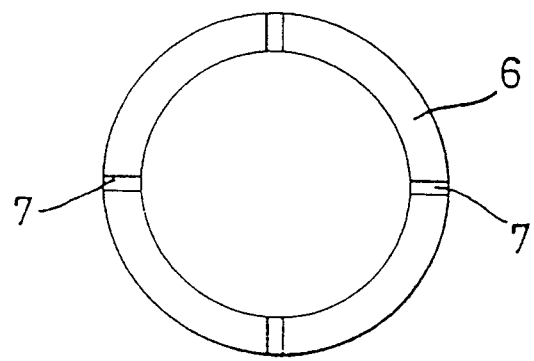
FIG. 2 is a plan showing a leak-controlling sheet in said first preferred embodiment.
Figure 3:
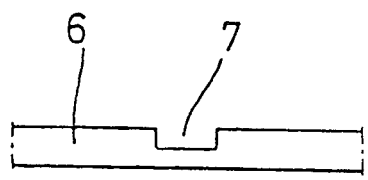
FIG. 3 is an enlarged front view showing main parts of said leak-controlling sheet in the first preferred embodiment.

The first preferred embodiment of the pneumatic infrared ray detector for use in a gas analyzer according to the present invention will be below described with reference to FIGS. 1 to 3. Referring to FIGS. 1 to 3, reference numeral 6 designates a ring-shaped leak-controlling sheet made of stainless steel. Said ring-shaped leak-controlling sheet 6 is provided with a plurality of groove-like gas-leaking passages 7 all over the length between inner and outer circumferential edges thereof on a side thereof, as shown in FIGS. 2 to 3, and the sum total of sectional areas of these plural gas-leaking passages 7 is set so as to correspond to a quantity of gas to be slowly leaked. Although these gas-leaking passages 7 can be simply formed in high accuracy, for example, by etching, means for forming the gas-leaking passages 7 can be optionally selected depending upon materials for forming the leak-controlling sheet 6 and the like.

Reference numeral 1 designates a body made of metals. The leak-controlling sheet 6 is built up on a bottom surface 3a of a detecting gas chamber 3 provided in said body 1 and a ring-shaped member 8 is built up on the leak-controlling sheet 6. And, since the gas-leaking passages 7 of the leak-controlling sheet 6 are arranged on the side opposite to said member 8, a gas-slowly leaking mechanism by means of the gas-leaking passages 7 is formed between the leak-controlling sheet 6 and the member 8. Reference numeral 10 designates a vibrating diaphragm made of a titanium foil and the like built up on the member 8. Since other constructions are the same as those in the conventional example shown in FIG. 9, they are designated by the same reference numerals as in FIG. 9 and their detailed description is omitted.

When a difference between gas pressures acting upon both sides of said vibrating diaphragm 10 is produced due to a difference in quantity of light between infrared rays incident upon a gas chamber 2a and infrared rays incident upon a gas chamber 2b, a gas flows through the gas-leaking passages 7 to be slowly leaked, whereby balancing said gas pressures acting upon both sides of the vibrating diaphragm 10. Although said gas is slowly leaked through the gas-leaking passages 7 provided in the leak-controlling sheet 6 in the above-described manner, this gas-leaking passages 7 can be optionally set in sectional area in high accuracy on the basis of a depth and a width thereof, so that a quantity of gas to be leaked can be consciously controlled in high accuracy and a range capable of controlling it can be increased.

In addition, although the gas-leaking passages 7 of the leak-controlling sheet 6 are arranged on the side of the member 8, they may be arranged on the side of the bottom surface 3a of the detecting gas chamber 3. Also a position where the leak-controlling sheet 6 is arranged can be optionally selected; for example, it may be brought into immediate contact with a surface of said vibrating diaphragm 10. And, since the pneumatic infrared ray detector for use in a double cell-type gas analyzer provided with a reference cell and a sample cell is described in the first preferred embodiment, infrared rays transmitting through said reference cell are incident on one of the gas chambers 2a, 2b while infrared rays transmitting through said sample cell are incident upon the other of the gas chambers 2a, 2b. However, the present invention can be applied also to a pneumatic infrared ray detector, in which a pair of gas chambers is arranged in optical series to an infrared ray source and a sample cell of a gas analyzer comprising merely said sample cell, such as the Unol-type gas analyzer, and infrared rays transmitting through the sample cell transmit through said gas chamber on the upstream side followed by being incident upon said gas chamber on the downstream side.

Figure 4:
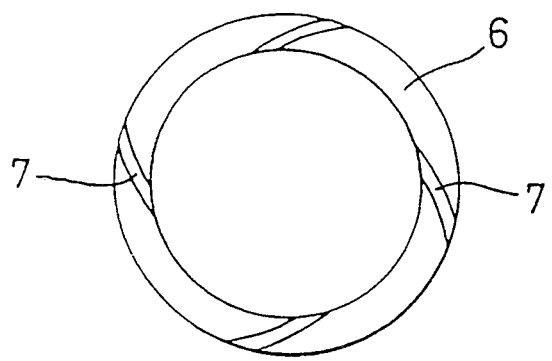
FIG. 4 is a plan showing a leak-controlling sheet in a second preferred embodiment.

FIG. 4 shows the second preferred embodiment and relates to the leak-controlling sheet 6. In the leak-controlling sheet 6 according to this second preferred embodiment, gas-leaking passages 7 thereof are inclined relatively to a radial direction of the leak-controlling sheet 6 and thus a length of the gas-leaking passages 7 can be increased. And, portions of the gas-leaking passages 7 are reduced in thickness but the thin-wall portions intersect said radial direction of the leak-controlling sheet 6, so that not only the leak-controlling sheet 6 can be prevented from being bent at said portions of the gas-leaking passages 7 when it is handled but also the leak-controlling sheet 6 can be smoothly and easily handled when it is produced or assembled.

In addition, in this second preferred embodiment, the gas-leaking passages 7 can be optionally arranged on one side or both sides of the leak-controlling sheet 6 and selected in number, sectional form and the like.

Figure 5:
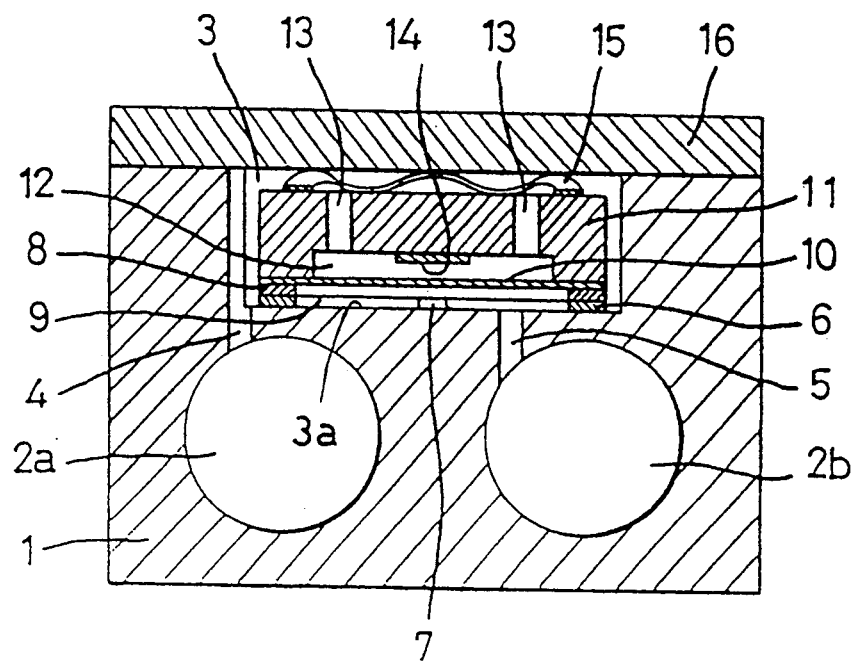
FIG. 5 is a block diagram showing a third preferred embodiment of the present invention.
Figure 6:
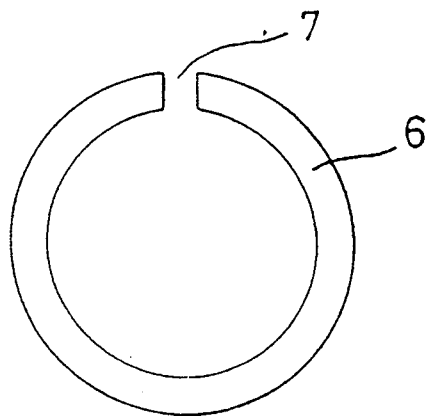
FIG. 6 is a plan showing a leak-controlling sheet in said third preferred embodiment.
Figure 7:
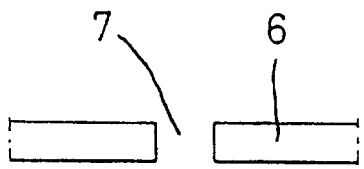
FIG. 7 is an enlarged front view showing main parts of said leak-controlling sheet in the third preferred embodiment.

The third preferred embodiment will be below described with reference to FIGS. 5 to 7. Referring to FIGS. 5 to 7, reference numeral 6 designates a ring-shaped leak-controlling sheet made of stainless steel. Said ring-shaped leak-controlling sheet 6 is provided with a gas-leaking passage 7 formed by removing a part thereof all over the length between inner and outer circumferential edges thereof, as shown in FIGS. 5 to 7, and a sectional area of this gas-leaking passage 7 is set so as to correspond to a quantity of gas to be slowly leaked. Although this gas-leaking passage 7 can be formed in high accuracy by, for example, etching, means for forming the gas-leaking passage 7 can be optionally selected depending upon materials for forming the leak-controlling sheet 6 and the like.

Figure 9:
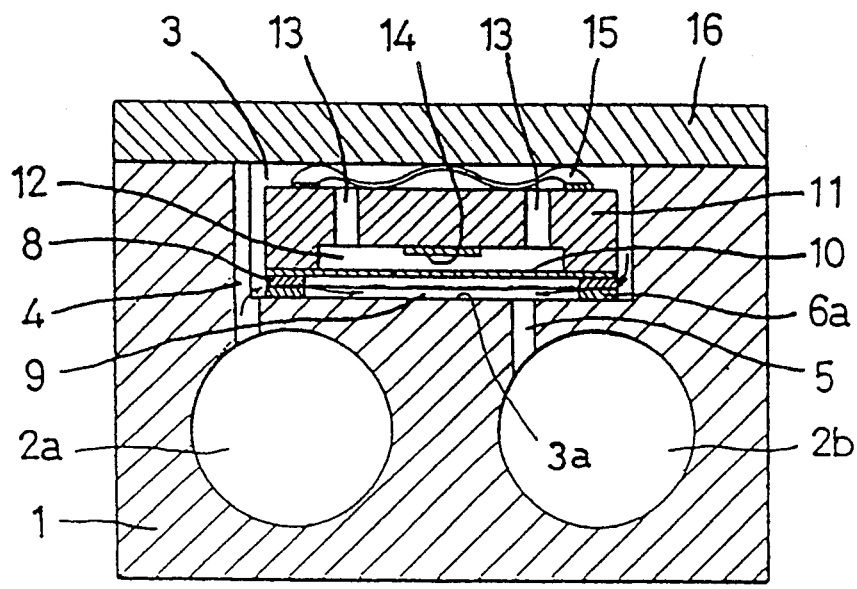
FIG. 9 is a diagram showing the conventional example.
Figure 10:
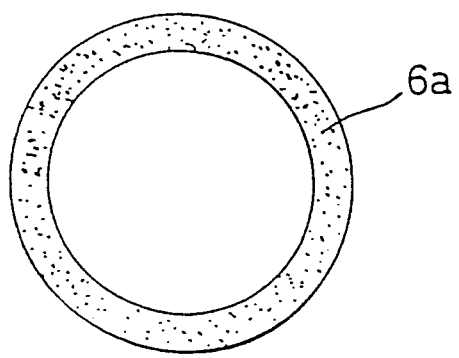
FIG. 10 is a plan showing a leak-controlling sheet in the conventional example.

Since other constructions are the same as those in the conventional example shown in FIG. 9, they are designated by the same reference numerals as in FIG. 9 and their detailed description is omitted.

Figure 8:
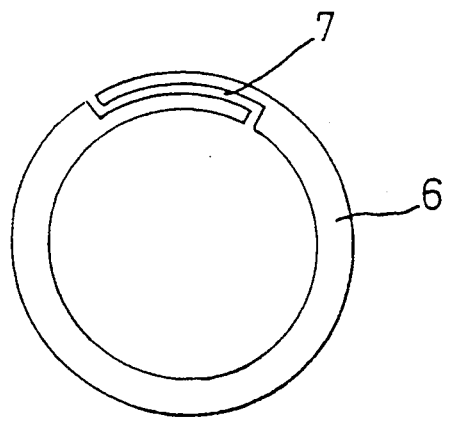
FIG. 8 is a plan showing a leak-controlling sheet in a fourth preferred embodiment.

FIG. 8 shows the fourth preferred embodiment. In a leak-controlling sheet 6 according to this fourth preferred embodiment, a long gas-leaking passage 7 is formed in a circumferential direction in a middle portion in the direction of width of the leak-controlling sheet 6 and one end thereof is opened in an outer circumferential edge of the leak-controlling sheet 6. Accordingly, the gas-leaking passage according to this fourth preferred embodiment can be formed in an almost optional length and a quantity of gas to be slowly leaked can be controlled by a sectional area and a length of the gas-leaking passage 7, so that said quantity of gas to be slowly leaked can be controlled more easily so as to be less.

As clear from the first to fourth preferred embodiments, the direction of the gas-leaking passage 7 relatively to the leak-controlling sheet 6 can be optionally selected.

Consequently, an optional quantity of gas can be slowly leaked in high accuracy by selecting the sectional area and the direction relatively to the leak-controlling sheet 6 of the gas-leaking passages 7.

According to the present invention, not only the sectional area of the gas-leaking passages can be optionally set in high accuracy but also it is hardly changed even if the leak-controlling sheet is pressurized from both sides, so that the quantity of gas to be slowly leaked can be controlled in high accuracy and also the range capable of controlling the quantity of gas to be slowly leaked can be increased and thus the optional quantity of gas can be slowly leaked. Accordingly, the pneumatic infrared ray detector for use in a gas analyzer superior in sensitivity and frequently characteristic can be provided.

What is claimed is:

1. A pneumatic infrared ray detector for use in a gas analyzer, in which a pair of gas chambers upon which infrared rays are incident, is provided in a body, a gas passage being formed for communicating said pair of gas chambers with each other, a vibrating diaphragm cutting off said gas passage fixedly mounted on said body and having its circumferential edge portion supported from both sides, and a mechanism for communicating respective portions of said gas passage cut off by said vibrating diaphragm to slowly leak gases enclosed in the respective gas chambers so provided;

characterized in that a ring-shaped leak-controlling sheet built up over the circumferential edge portion on one side of said vibrating diaphragm is provided with at least one groove-shaped gas-leaking passage formed between an inner circumferential edge and an outer circumferential edge thereof and one of said respective portions of said gas passage cut off by said vibrating diaphragm is provided on an outer circumferential side of said leak-controlling sheet while the other of said respective portions of said gas passage cut off by said vibrating diaphragm is provided on an inner circumferential side of said leak-controlling sheet.

2. The pneumatic infrared ray detector of claim 1 wherein said ring-shaped leak-controlling sheet is made of metal.

3. The pneumatic infrared ray detector of claim 2 wherein said metal is selected from the group consisting of stainless steel or aluminum.

4. The pneumatic infrared ray detector of claim 1 wherein said ring-shaped leak-controlling sheet is made of plastic.

5. The pneumatic infrared ray detector of claim 4 wherein said plastic is polytetrafluoroethylene.

6. The pneumatic infrared ray detector of claim 1 wherein said at least one groove-shaped gas-leaking passage comprises a plurality of generally radially arrayed grooves having a total sectional area corresponding to a quantity of gas to be slowly leaked.

7. The pneumatic infrared ray detector of claim 1 wherein said at least one groove-shaped gas-leaking passage comprises at least one slot having a total sectional area corresponding to a quantity of gas to be slowly leaked.

8. The pneumatic infrared ray detector of claim 1 wherein said at least one groove-shaped gas-leaking passage comprises at least one circumferentially disposed passage having one end opened to the outer circumferential side of said leak-controlling sheet and the other end opened to the inner circumferential side of said leak-controlling sheet and having a total sectional area corresponding to a quantity of gas to be slowly leaked.

9. A pneumatic infrared ray detector for use in a gas analyzer, said detector comprising:

a body provided with a pair of gas chambers and a gas passage connected therebetween;

a vibrating diaphragm having a peripheral edge portion fixedly mounted on said body and sealingly cutting off said gas passage; and a leak-controlling sheet sealingly disposed on said peripheral edge portion of said vibrating diaphragm and provided with at least one groove-shaped gas-leaking passage having a sectional area corresponding to a quantity of gas to be slowly leaked past said vibrating diaphragm and between said gas chambers.

10. The pneumatic infrared ray detector of claim 9 wherein said vibrating diaphragm is ring-shaped and said at least one groove-shaped gas-leaking passage extends between the inner circumferential edge of said ring-shaped leak-controlling sheet and the outer circumferential edge thereof.

11. The pneumatic infrared ray detector of claim 10 wherein said ring-shaped leak-controlling sheet is made of metal.

12. The pneumatic infrared ray detector of claim 11 wherein said metal is selected from the group consisting of stainless steel or aluminum.

13. The pneumatic infrared ray detector of claim 10 wherein said ring-shaped leak-controlling sheet is made of plastic.

14. The pneumatic infrared ray detector of claim 13 wherein said plastic is polytetrafluoroethylene.

15. The pneumatic infrared ray detector of claim 9 wherein said at least one groove-shaped gas-leaking passage comprises a plurality of generally radially arrayed grooves having a total sectional area corresponding to a quantity of gas to be slowly leaked.

16. The pneumatic infrared ray detector of claim 9 wherein said at least one groove-shaped gas-leaking passage comprises at least one slot having a total sectional area corresponding to a quantity of gas to be slowly leaked.

17. The pneumatic infrared ray detector of claim 10 wherein said at least one groove-shaped gas-leaking passage comprises at least one circumferentially disposed passage having one end opened to the outer circumferential side of said leak-controlling sheet and the other end opened to the inner circumferential side of said leak-controlling sheet and having a total sectional area corresponding to a quantity of gas to be slowly leaked.

18. A leak-controlling sheet for use in a pneumatic infrared ray detector having a vibrating diaphragm sealingly cutting off a gas passage connecting a pair of gas chambers, said leak-controlling sheet comprising:

a ring-shaped sheet disposed about the periphery of said vibrating diaphragm and provided with at least one groove-shaped gas-leaking passage having a sectional area corresponding to a quantity of gas to be slowly leaked.

19. The leak-controlling sheet of claim 18 wherein said at least one groove-shaped gas-leaking passage comprises a plurality of generally radially arrayed grooves having a total sectional area corresponding to a quantity of gas to be slowly leaked.

20. The leak-controlling sheet of claim 18 wherein said at least one groove-shaped gas-leaking passage comprises at least one slot having a total sectional area corresponding to a quantity of gas to be slowly leaked.

21. The leak-controlling sheet of claim 18 wherein said at least one groove-shaped gas-leaking passage comprises at least one circumferentially disposed passage having one end opened to the outer circumferential side of said leak-controlling sheet and the other end opened to the inner circumferential side of said leak-controlling sheet and having a total sectional area corresponding to a quantity of gas to be slowly leaked.

* * * * *